US012569096B2

(12) United States Patent

Molina Cabrera et al.

(10) Patent No.: US 12,569,096 B2

(45) Date of Patent: Mar. 10, 2026

(54) SYSTEM AND METHOD OF SOFTWARE AND PITCH CONTROL OF A DISINFECTION MODULE FOR A SEMI-AUTONOMOUS CLEANING AND DISINFECTION DEVICE

(71) Applicant: Avidbots Corp, Kitchener (CA)

(72) Inventors: Pablo Roberto Molina Cabrera, Waterloo (CA); Kenneth King Ho Lee, Mississauga (CA); Cameron Scott Reidlinger Fraser, Kitchener (CA); Florin Coca, Kitchener (CA)

(73) Assignee: AVIDBOTS CORP

( * ) Notice: Subject to any disclaimer, the term of this patent is extended or adjusted under 35 U.S.C. 154(b) by 0 days.

(21) Appl. No.: 17/664,765

(22) Filed: May 24, 2022

(65) Prior Publication Data

US 2022/0296058 A1     Sep. 22, 2022

Related U.S. Application Data

(60) Provisional application No. 63/192,553, filed on May 24, 2021.

(51) Int. Cl.
| | |
|---|---|
| *A47L 7/00* | (2006.01) |
| *A47L 9/00* | (2006.01) |
| *A47L 9/28* | (2006.01) |
| *A47L 11/40* | (2006.01) |
| *A61L 2/22* | (2006.01) |
| *A61L 2/24* | (2006.01) |

(52) U.S. Cl.
CPC ............. *A47L 7/0061* (2013.01); *A47L 9/009* (2013.01); *A47L 9/2826* (2013.01); (Continued)

(58) Field of Classification Search
CPC ...... A47L 7/0061; A47L 9/009; A47L 9/2826; A47L 9/2847; A47L 9/2852; (Continued)

(56) References Cited

U.S. PATENT DOCUMENTS

| | | | | | |
|---|---|---|---|---|---|
| 2013/0327353 | A1* | 12/2013 | Field | .......................... | B08B 7/00 134/1 |
| 2016/0309973 | A1* | 10/2016 | Sheikh | ................ | A47L 11/4066 |

(Continued)

FOREIGN PATENT DOCUMENTS

| | | | | | |
|---|---|---|---|---|---|
| CN | 111265707 | A | * | 6/2020 | ............... A61L 9/14 |
| CN | 111331612 | A | * | 6/2020 | |

(Continued)

OTHER PUBLICATIONS

Translation of WO-2021208381-A1 (Year: 2021).*

(Continued)

*Primary Examiner* — David S Posigian
*Assistant Examiner* — Steven Huang

(57) ABSTRACT

A system and method of software control and autonomy of a disinfection module for an autonomous or semi-autonomous cleaning device. The disinfection module control software resides on a computer with processor and memory. The disinfection module is connected to peripherals for sensing and localizing in the environment and controlling the actuators for the motion of the cleaning device. The disinfection module control software processes the sprayer's status, follows and plans paths to move the cleaning device to the spray targets, generates appropriate motion commands, and controls the disinfection module's pump, fan, LED, and electrostatic generator states.

7 Claims, 16 Drawing Sheets

(52) U.S. Cl.
CPC .......... *A47L 9/2847* (2013.01); *A47L 9/2852*
(2013.01); *A47L 9/2857* (2013.01); *A47L*
*11/4008* (2013.01); *A47L 11/4011* (2013.01);
*A47L 11/4066* (2013.01); *A47L 11/4088*
(2013.01); *A61L 2/22* (2013.01); *A61L 2/24*
(2013.01); *A47L 2201/04* (2013.01); *A47L*
*2201/06* (2013.01); *A61L 2202/14* (2013.01);
*A61L 2202/15* (2013.01); *A61L 2202/16*
(2013.01); *A61L 2202/17* (2013.01); *A61L*
*2202/25* (2013.01)

(58) Field of Classification Search
CPC .......................... A47L 9/2857; A47L 11/4008;
A47L 11/4011; A47L 11/4066; A47L
11/4088; A47L 11/40; A47L 11/4013;
A47L 11/16; A47L 11/408; A47L
2201/04; A47L 2201/06; A61L 2/22;
A61L 2/24; A61L 2202/14; A61L
2202/15; A61L 2202/16; A61L 2202/17;
A61L 2202/25
See application file for complete search history.

(56) References Cited

U.S. PATENT DOCUMENTS

| 2017/0049288 A1* | 2/2017 | Knutson | ............. A47L 11/4083 |
| 2019/0179307 A1* | 6/2019 | Anderson | ............ G05D 1/0061 |
| 2020/0379096 A1* | 12/2020 | Zhou | ..................... G01S 7/4802 |

FOREIGN PATENT DOCUMENTS

| CN | 112426101 A | * | 3/2021 | .......... A47L 11/4088 |
| KR | 102156511 B1 | * | 9/2015 | |
| WO | WO-2021208381 A1 | * | 10/2021 | ............... A61L 2/22 |

OTHER PUBLICATIONS

Definition of Computer, Merriam-Webster (Year: 2015).*
Translation of CN 111265707 A (Year: 2020).*
Translation of CN 111331612 A (Year: 2020).*
The Benefits of Finite State Machines, archived Mar. 12, 2020, from
"https://www.crossmuller.com.au/news/the-benefits-of-finite-state-
machines-in-industrial-automation/" (Year: 2020).*
Translation of CN 112426101 A (Year: 2021).*

* cited by examiner

1300

1302

1304

1306    1308    1310            1312        1314            1316

1400

1402

1404

1410    1408    1406

1600

1602

1604

1606     1608     1610

1700

1702

1704

1706     1708

SYSTEM AND METHOD OF SOFTWARE AND PITCH CONTROL OF A DISINFECTION MODULE FOR A SEMI-AUTONOMOUS CLEANING AND DISINFECTION DEVICE

CROSS REFERENCE TO RELATED APPLICATIONS

The application claims priority to and the benefit of U.S. Provisional Patent Application Ser. No. 63/192,553, entitled "SYSTEM AND METHOD OF SOFTWARE AND PITCH CONTROL OF A DISINFECTION MODULE FOR A SEMI-AUTONOMOUS CLEANING AND DISINFECTION DEVICE" filed on May 24, 2021, the disclosure of which are incorporated herein by reference in their entirety.

BACKGROUND

The embodiments described herein relate to semi-autonomous cleaning and disinfection devices and more particularly, to a system and method for a disinfection module for a semi-autonomous cleaning device for cleaning surfaces.

There is a problem in the janitorial industry where business facilities must quickly adopt a quality disinfection solution while easing the risk and burden of their human cleaning staff. One solution is to use an autonomous or semi-autonomous cleaning device with a disinfection module upgrade that can automatically disinfect facilities without human intervention. However, even with the assistance of autonomous or semi-autonomous cleaning device there is requirement for precision autonomous control.

There is a need for precision autonomous control (e.g., start, stop, constant travel speed, adjustable flow rate, etc.) of a disinfection module attached to an autonomous or semi-autonomous cleaning device Neo™. The disinfection module is used to spray disinfectant solution evenly on a variety of surfaces in different cleaning areas (e.g., schools, airports, shopping malls, etc.) as the cleaning device is cleaning the floor surfaces of the cleaning area.

In the case of disinfection, these are various touch points (e.g., handrails, door handles, lockers, electronic terminals, refuse bins, tables, chairs, benches, countertops, etc.) that require disinfection.

Autonomous disinfection has several benefits, including:

No personnel needed in the environment, which reduces exposure to and spread of health and safety risks (e.g., COVID-19).

Accurate and detailed reporting of disinfection operations.

Repeatable and consistent performance.

Time savings for personnel who do not have time to perform all necessary sanitation tasks.

Precision control entails the coordination of sprayer actuation and deactivation with the mobile cleaning device's position, orientation, and speed in a mapped environment with annotated targets, alongside timely visual and audible alerts to passersby (i.e., people or other machines). Further, the device must safely and gracefully handle dynamic obstructions that may occlude the spray target.

Being an easy-to-use autonomous solution, diagnostic capabilities are essential to understanding the working state of the disinfection module in both manual and autonomous operation modes. Reporting capabilities are also a key component of an autonomous disinfection system, to track usage, spray coverage, and success.

Software configuration and design allows the cleaning device to perform both cleaning and disinfecting, potentially simultaneously. This has the benefit of a higher return on investment (ROI) since the cleaning device is achieving more goals in a shorter amount of time with a single machine.

Robotic disinfection devices exist, however, typically these devices blanket the coverage area and may not achieve adequate disinfection levels (i.e., dwell time and concentration). Furthermore, these solutions may also be wasteful with their discharge of disinfectant solution (i.e., the disinfection solution may spray everywhere and land on non-touch point areas). Ultraviolet (UV) light-based disinfection devices are also used for disinfection, but these devices are unable to disinfect behind occlusions of the UV emitter, leaving gaps in coverage.

There is a desire for autonomous precision control of a disinfection module by an autonomous or semi-autonomous cleaning device. There is a further desire that the cleaning device can also perform both cleaning and disinfecting procedures using software control.

SUMMARY

A system and method of software control and autonomy of a disinfection module for an autonomous or semi-autonomous cleaning device. The disinfection module control software resides on a computer with a processor and memory. The disinfection module is connected to peripherals for sensing and localizing in the environment and controlling the actuators for the motion of the cleaning device. The disinfection module control software processes the sprayer's status, follows and plans paths to move the cleaning device to the spray targets, generates appropriate motion commands, and controls the disinfection module's pump, fan, LED, and electrostatic generator states.

DETAILED DESCRIPTION

Figure 1:
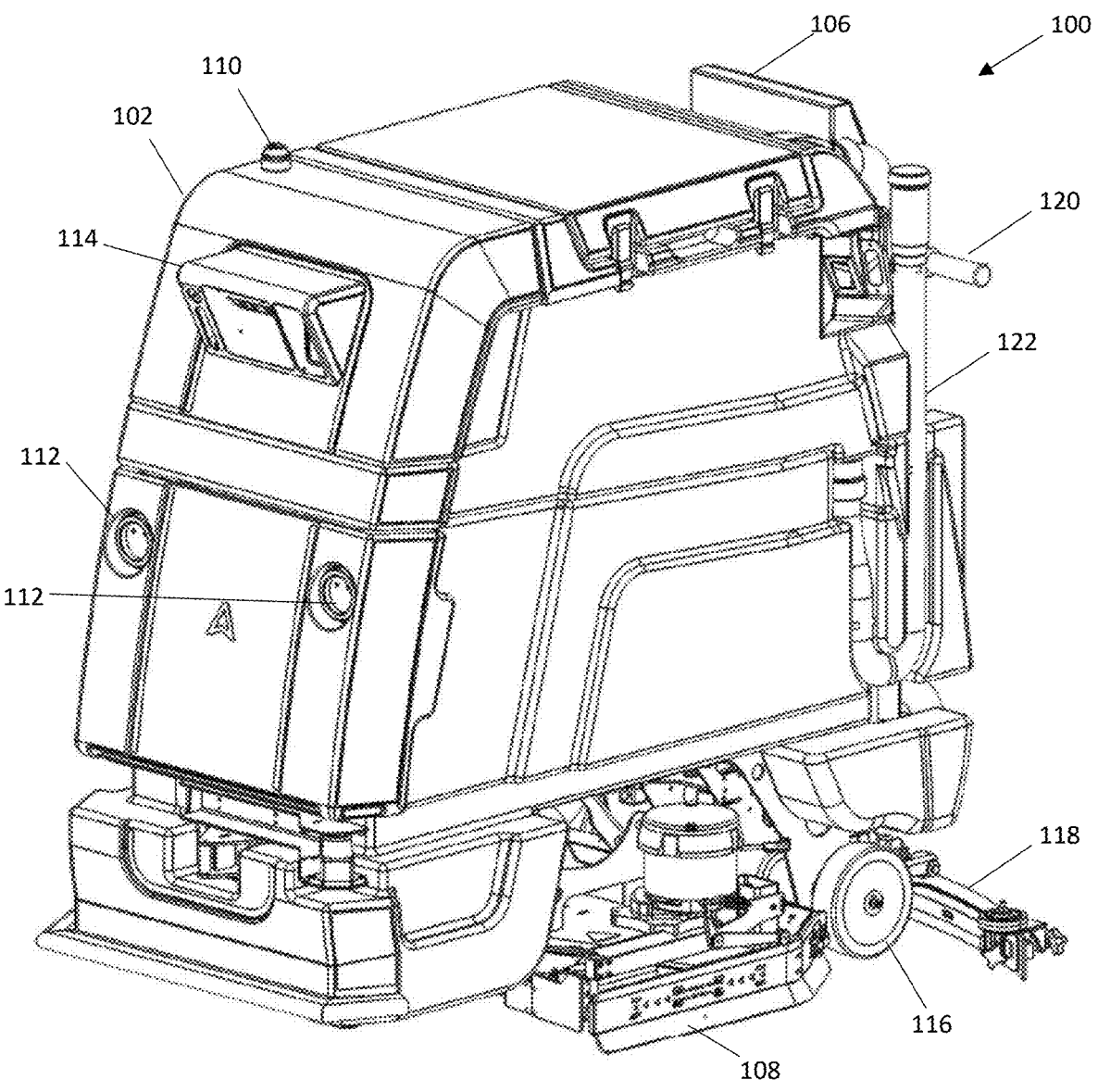
FIG. 1 is a perspective view of a semi-autonomous cleaning device.
Figure 2:
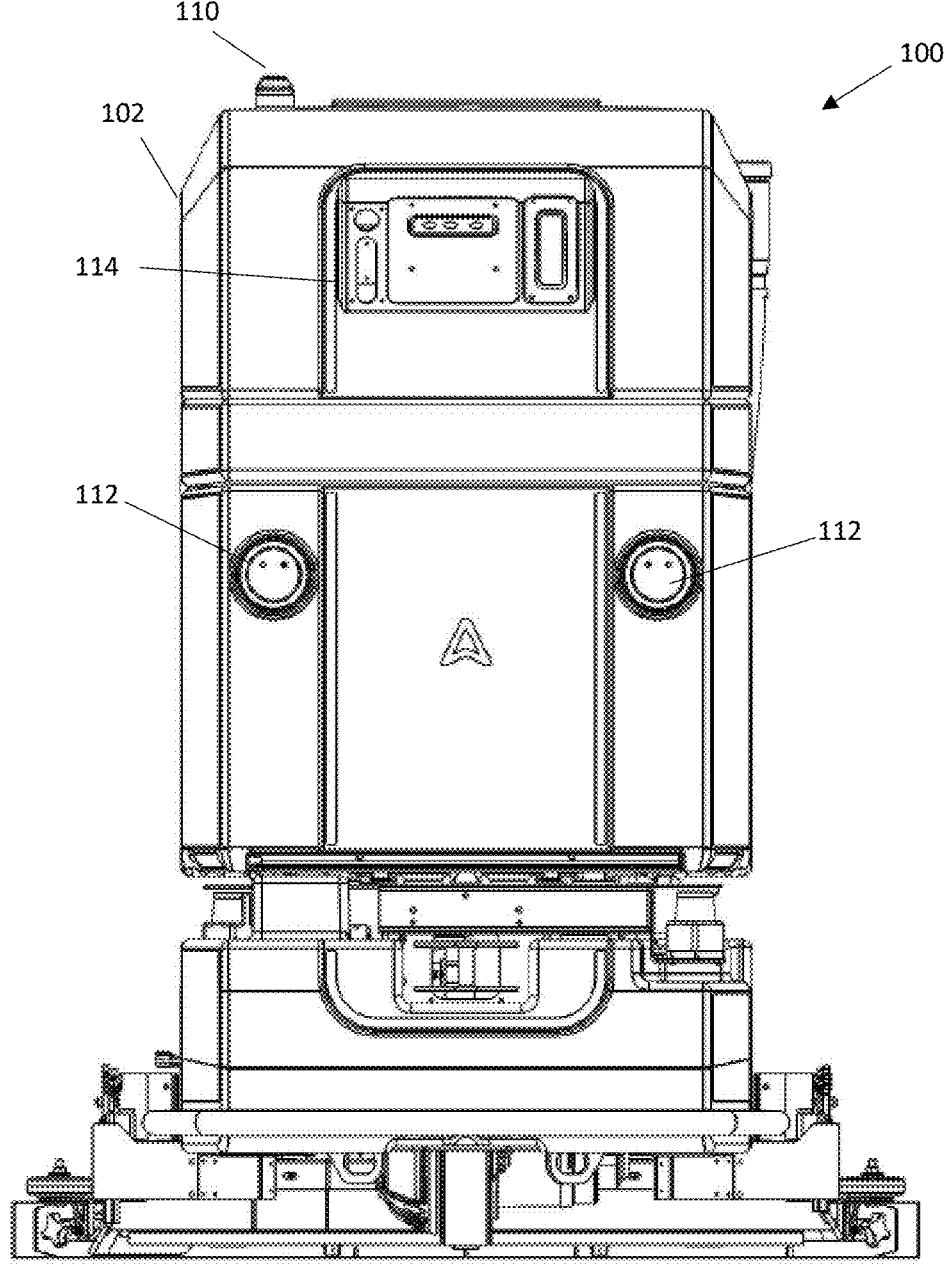
FIG. 2 is a front view of a semi-autonomous cleaning device.
Figure 3:
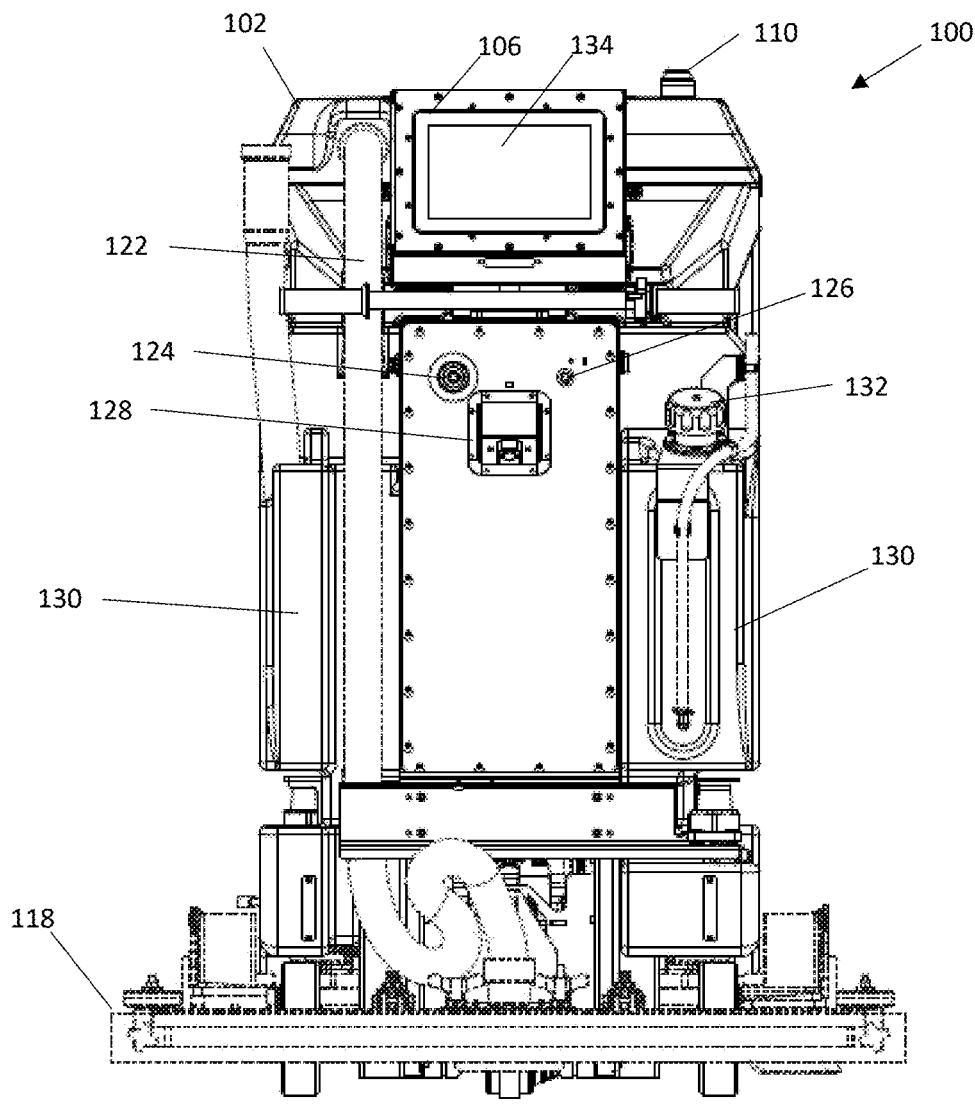
FIG. 3 is a back view of a semi-autonomous cleaning device.
Figure 4:
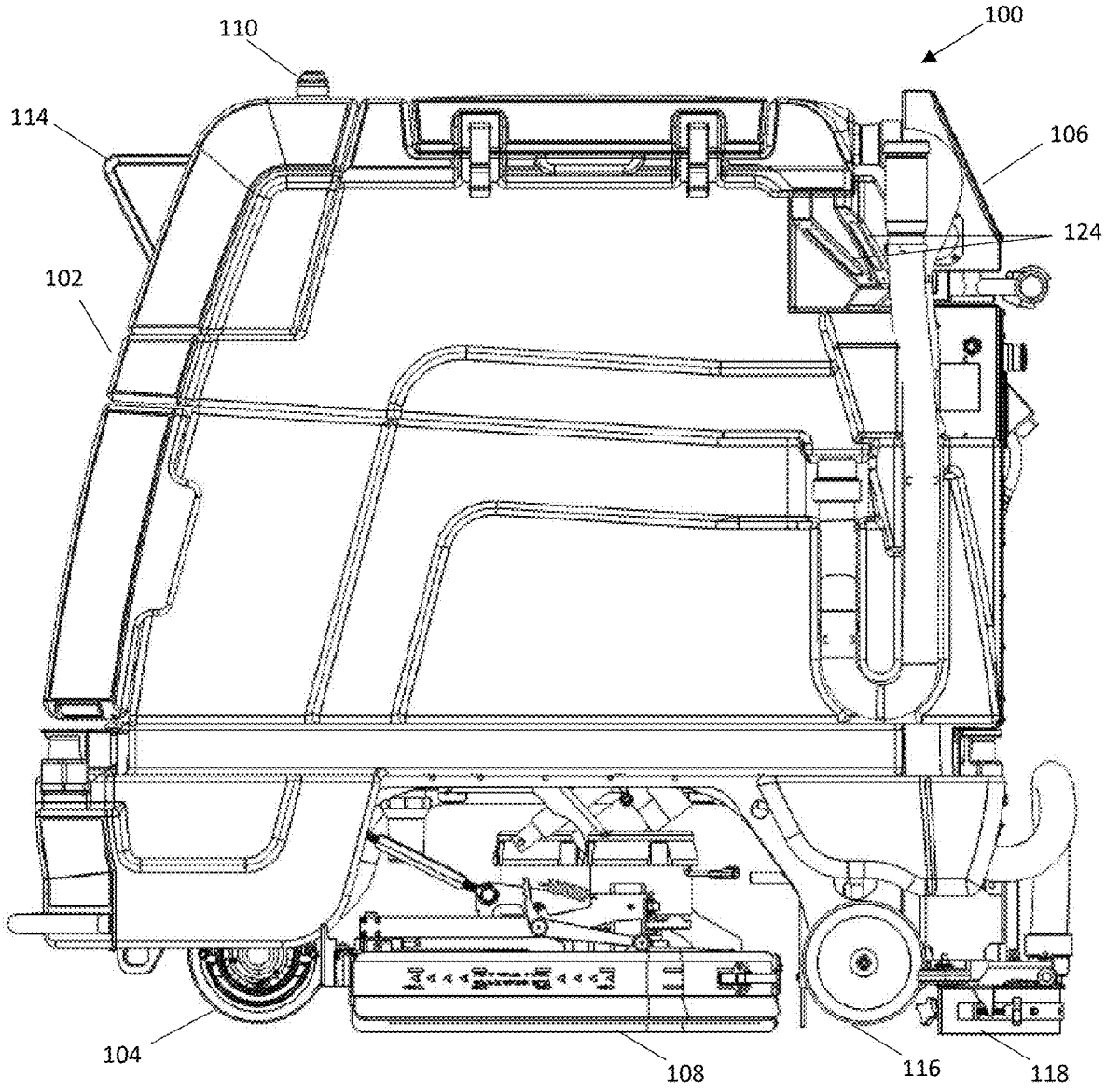
FIG. 4 is a left side view of a semi-autonomous cleaning device.
Figure 5:
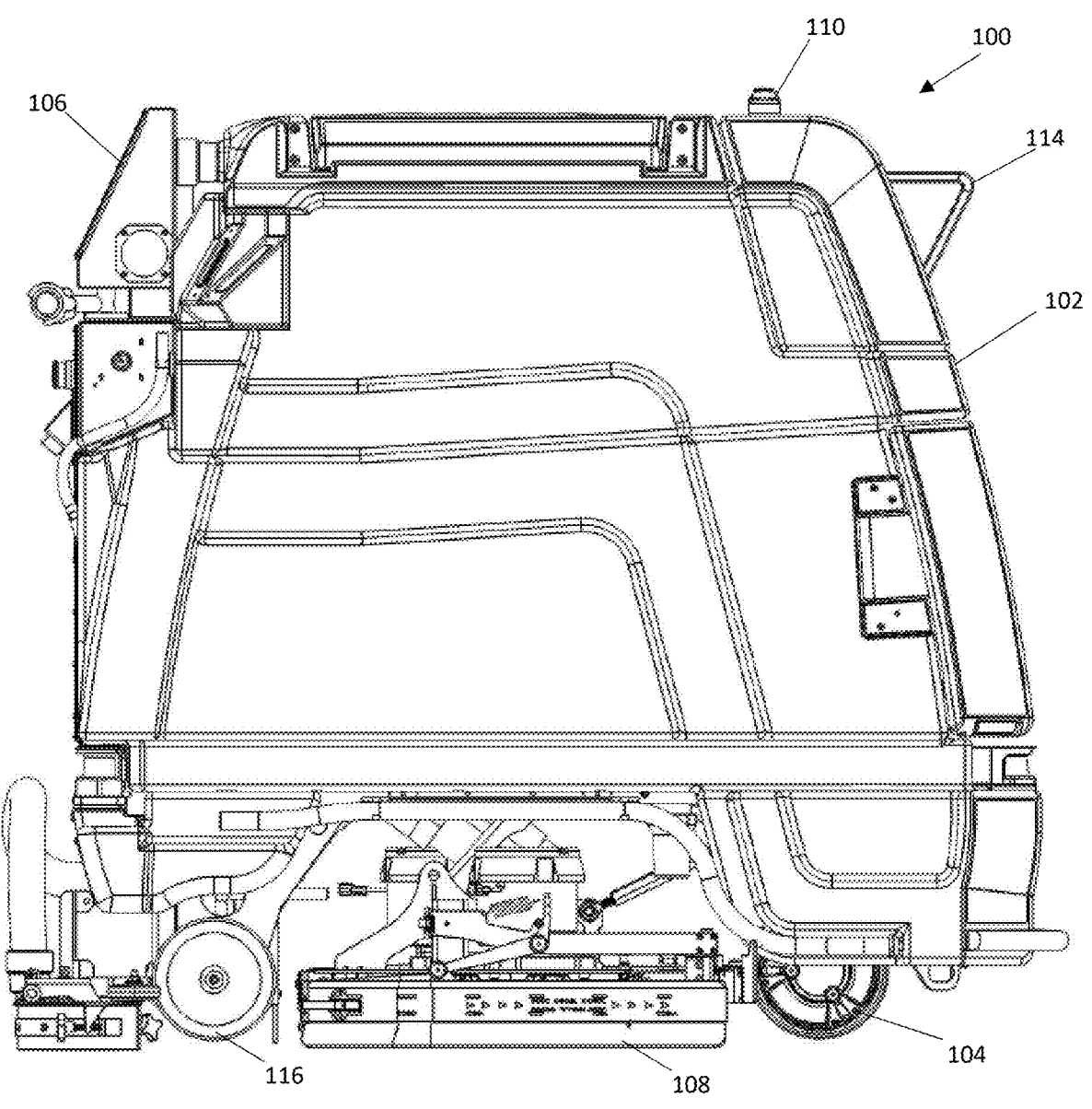
FIG. 5 is a right side view of a semi-autonomous cleaning device.

An exemplary embodiment of a semi-autonomous cleaning device is shown in FIGS. 1-5. FIG. 1 is a perspective view of a semi-autonomous cleaning device. FIG. 2 is a front view of a semi-autonomous cleaning device. FIG. 3 is a back view of a semi-autonomous cleaning device. FIG. 4 is a left side view of a semi-autonomous cleaning device, and FIG. 5 is a right side view of a semi-autonomous cleaning device.

FIGS. 1 to 5 illustrate a semi-autonomous cleaning device 100. The device 100 (also referred to herein as "cleaning device" or "cleaning robot") includes at least a frame 102, a drive system 104, an electronics system 106, and a cleaning assembly 108. The cleaning device 100 can be used to clean, vacuum, scrub and disinfect any suitable surface area such as, for example, a floor of a home, commercial building, warehouse, etc. The cleaning device 100 can be any suitable shape, size, or configuration and can include one or more systems, mechanisms, assemblies, or subassemblies that can perform any suitable function associated with, for example, traveling along a surface, mapping a surface, cleaning a surface, and/or the like.

The frame 102 of cleaning device 100 can be any suitable shape, size, and/or configuration. For example, in some embodiments, the frame 102 can include a set of components or the like, which are coupled to form a support structure configured to support the drive system 104, the cleaning assembly 108, and the electronic system 106. Cleaning assembly 108 may be connected directly to frame 102 or an alternate suitable support structure or sub-frame (not shown). The frame 102 of cleaning device 100 further comprises strobe light 110, front lights 112, a front sensing module 114 and a rear sensing module 128, side cameras 124, rear wheels 116, rear skirt 118, handle 120 and cleaning hose 122. The frame 102 also includes one or more internal storage tanks or storing volumes for storing water, disinfecting solutions (i.e., bleach, soap, cleaning liquid, etc.), debris (dirt), and dirty water. More information on the cleaning device 100 is further disclosed in PCT publication WO2016/168944, entitled "APPARATUS AND METHODS FOR SEMI-AUTONOMOUS CLEANING OF SURFACES" filed on Apr. 25, 2016 and International Application Serial No. PCT/CA2020/051100, entitled "SYSTEM AND METHOD OF SEMI-AUTONOMOUS CLEANING OF SURFACES", these disclosures of which are incorporated herein by reference in their entirety.

More particularly, in this embodiment, the front sensing module 114 further comprises structured light sensors in a vertical and horizontal mounting position, an active stereo sensor and an RGB camera. The rear sensing module 128, as seen in FIG. 3, consists of a rear optical camera. In further embodiments, front and rear sensing modules 114 and 128 may also include other sensors including one or more optical camera, thermal cameras, LiDAR (Light Detection and Ranging), structured light sensors, active stereo sensors (for 3D) and RGB cameras, etc.

The back view of a semi-autonomous cleaning device 100, as seen in FIG. 3, further shows frame 102, cleaning hose 122, clean water tank 130, clean water fill port 132, rear skirt 118, strobe light 110 and electronic system 106. Electronic system 106 further comprises display 134 which can be either a static display or touchscreen display. Rear skirt 118 consists of a squeegee head or rubber blade that engages the floor surface along which the cleaning device 100 travels and channels debris towards the cleaning assembly 108.

FIG. 3 further includes emergency stop button 124 which consists of a big red button, a device power switch button 126 and a rear sensing module 128. Rear sensing module 128 further comprises an optical camera that is positioned to sense the rear of device 100. This complements the front sensing module 114 which provides a view and direction of the front of device 100, which work together to sense obstacles and obstructions.

Figure 6:
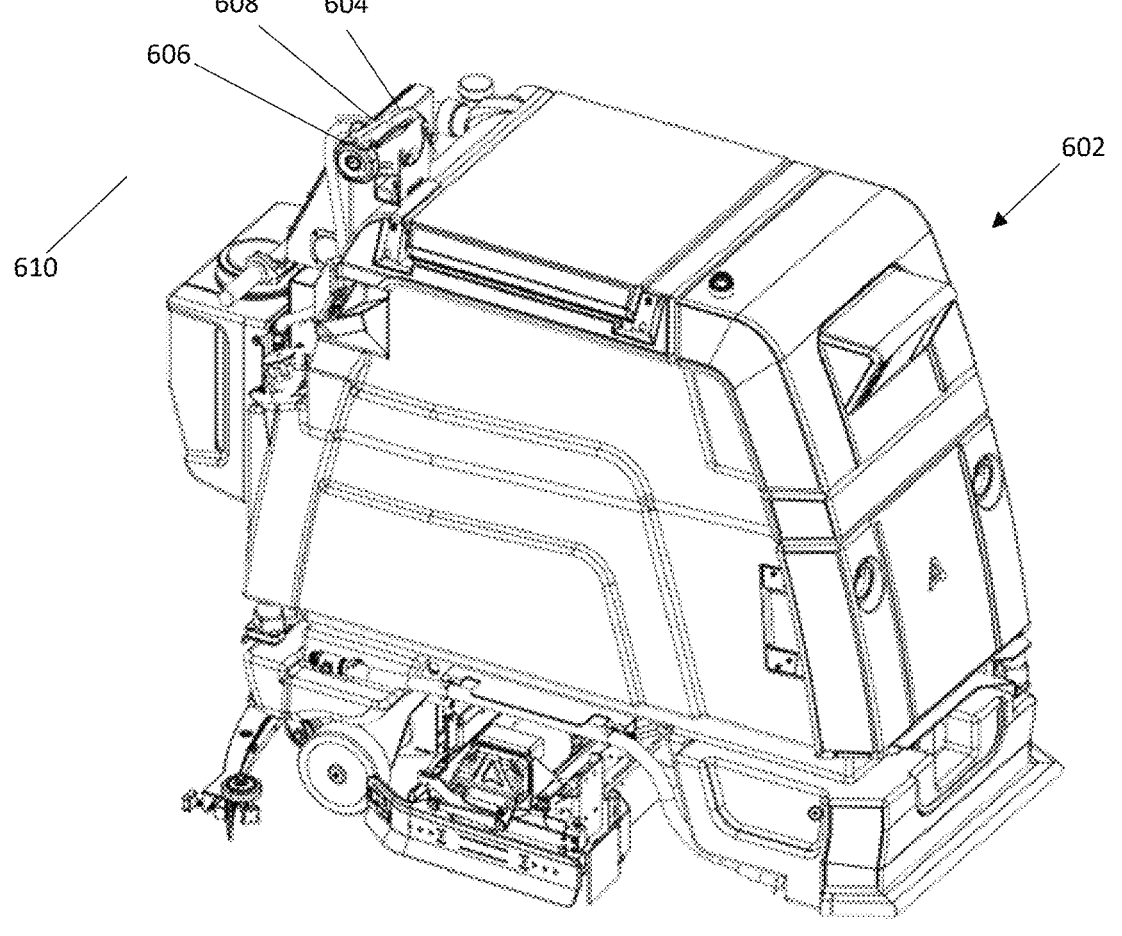
FIG. 6 is a perspective view of a semi-autonomous cleaning device with an external disinfection module.

FIG. 6 is a perspective view of a semi-autonomous cleaning device with an external disinfection module 602. As seen in FIG. 6, components of the disinfection module comprise of:

High powered fan (DC voltage) 604

Atomizer nozzle 606

Electrostatic module cathode

Electrostatic module 608

According to FIG. 6, the disinfection module consists of a spraying, misting and/or fogging system that will distribute a disinfectant solution 610 onto touch areas such as handles, doors, handrails, touchscreens, tables, countertops, shelves, and other areas that need regular disinfecting. The disinfection module will mount to a semi-autonomous cleaning device and will be able to automatically navigate to any location of the facility and disinfect it as needed using the automation and infrastructure of our existing product.

The disinfection module 602 may contain a solution tank, an atomizing system, a dispersion system, and an electrostatic system. The system will be mounted so the disinfectant solution 610 can spread at an appropriate height and within a 1.5 m distance from the cleaning device. By utilizing an electrostatic system, the module can maximize total coverage and disinfectant despite spray angle. Further info on the disinfection module can be found in the U.S. provisional application No. 63/055,919, entitled "DISINFECTION MODULE FOR A SEMI-AUTONOMOUS CLEANING AND DISINFECTION DEVICE", filed on Jul. 24, 2020, which is incorporated herein by reference in its entirety.

As seen in FIG. 6, the function of the disinfection module is to spray an electrostatically charged disinfection solution into an airstream and onto vertical/horizontal surfaces. These surfaces include washroom doors, handles, doorknobs, walls and entryways.

According to this disclosure, the disinfection solution would be any chemical that can be sprayed, commonly but not limited to quaternary ammonium, hydrogen peroxide, iso-propyl, and any other chemical or liquid that can be sprayed and recognized for having disinfecting properties. Furthermore, the disinfection solution may contain perfume, room fresheners and odor killing solutions (i.e., Febreze®).

Figure 7:
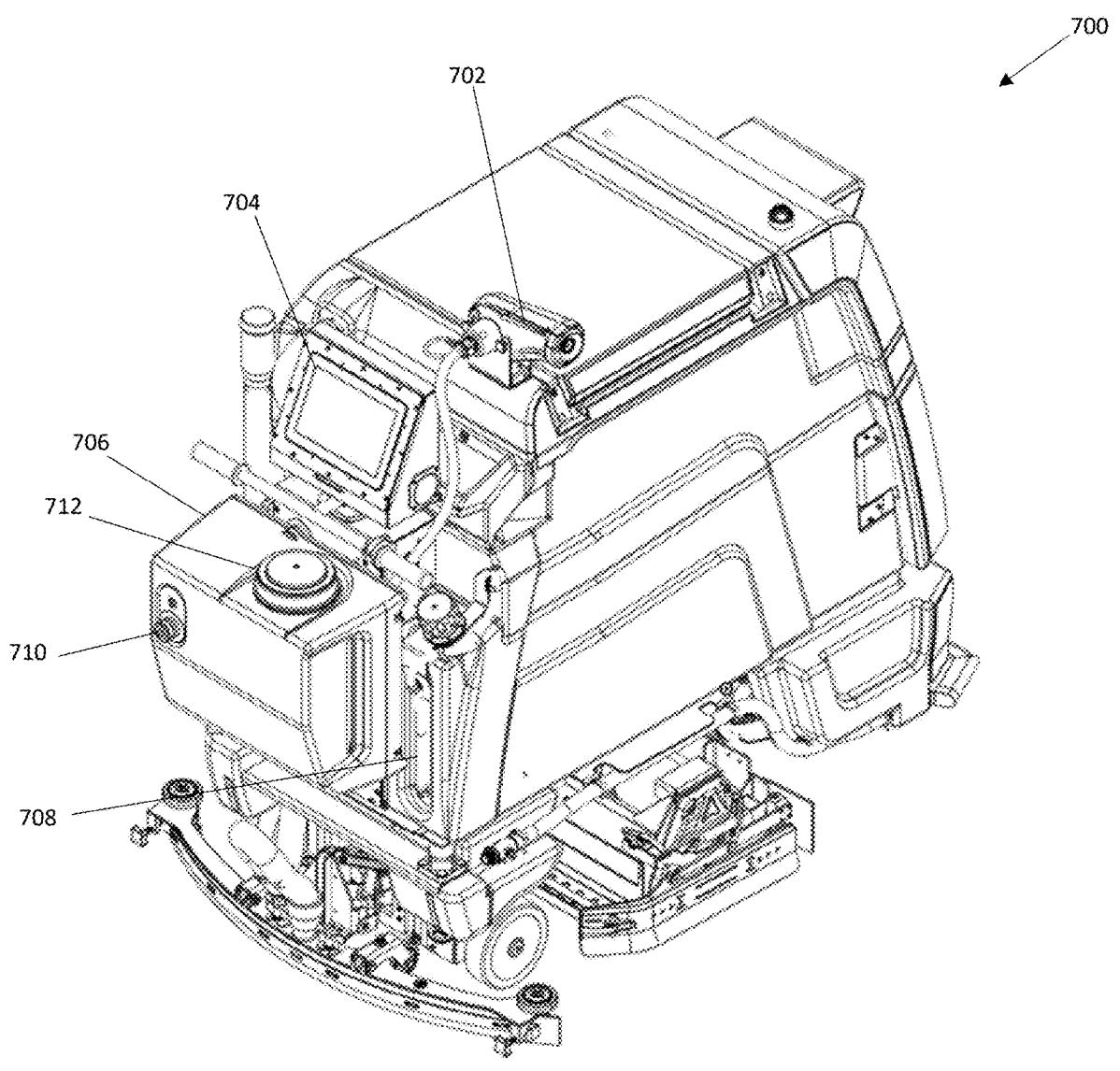
FIG. 7 is a further perspective view of a semi-autonomous cleaning device with another external disinfection module design.

FIG. 7 is a further perspective view of a semi-autonomous cleaning device with another external disinfection module design. According to FIG. 7, semi-autonomous cleaning device 700 comprises of sprayer 702, display 704, tank 706, clean water level indicator hose 708, emergency stop button 710 and pump 712. Pump 712 may be housed behind or enclosed inside tank 706.

Figure 8:
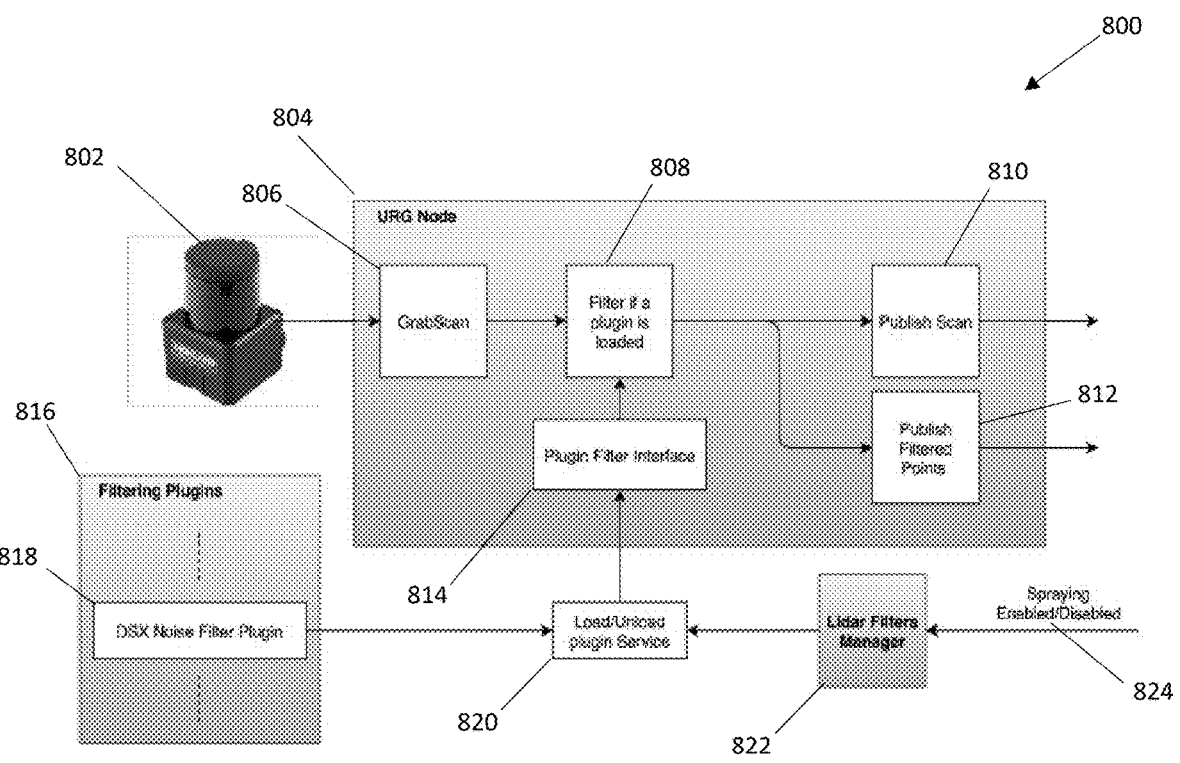
FIG. 8 is a diagram illustrating an exemplary LIDAR data processing architecture for the disinfection module.

FIG. 8 is a diagram illustrating an exemplary LIDAR data processing architecture for the disinfection module. According to FIG. 8, the LIDAR data processing architecture 800 is used for supporting modular plugins that can each apply different measurement filters, such as an intensity filter for filtering spray noise, which can be toggled on/off from external triggers such as spray on/off for safety reasons to only activate the filter when spraying to avoid false negatives (i.e., filtering out real obstacles).

According to FIG. 8, LIDAR module 802 communicates with URG node module 804 by first executing a GrabScan function 806. Thereafter, it determines whether to filter if a plugin is loaded at 808. If it is, the architecture 800 publishes the scan at 810 and publishes filtered points at 812.

According to FIG. 8, architecture 800 also consists of plugin service 820 that loads and unload filtering plugins 816. Filtering plugins further comprises DSX noise filter plugin 818. Alternately, architecture 800 determines whether spraying is enabled/disabled at 824 whereby it connects to a LIDAR filters manager 822 and also connects to the load/unload plugin service 820. The next step is to connect to the plugin filter interface 814 whereby it loops back and connects to step 808 (filter if a plugin is loaded).

Figure 9:
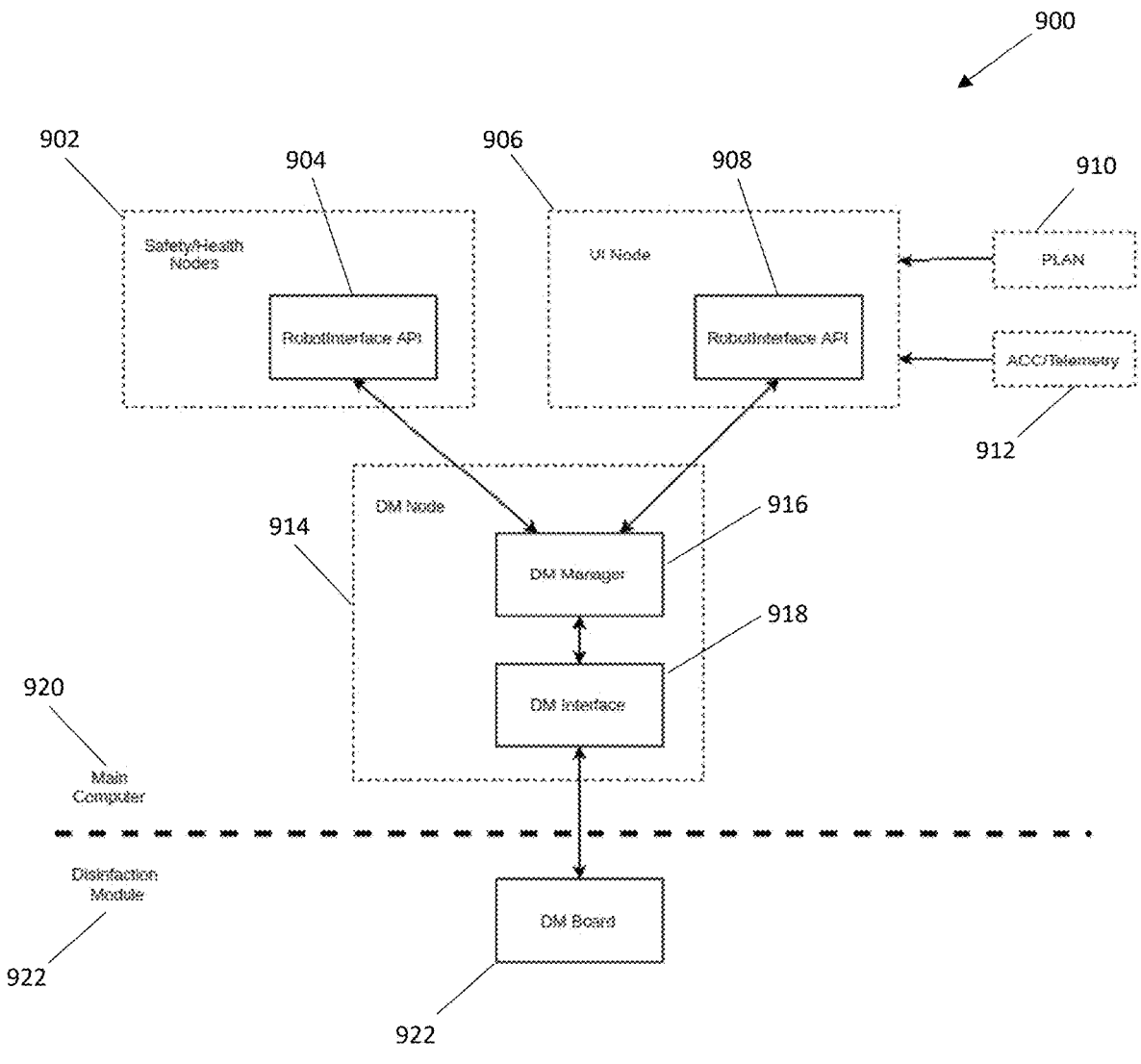
FIG. 9 is a diagram illustrating the spray settings architecture for the disinfection module.

FIG. 9 is a diagram illustrating spray settings architecture for the disinfection module. According to FIG. 9, spray settings architecture 900 is a simplified view of the different sources of setting the sprayer on/off. The different sources include the safety system, the remote monitoring system (i.e., Command Center controlling the command and telemetry system), and the autonomy system. There is additionally one other source which is the operator who interacts physically directly with the cleaning device via the diagnostics user interface (UI). The disinfection module (DM) manager decides which setting to accept, and sends it to the DM software/hardware interface on the main computer, to be converted to a signal (over 10/100 Ethernet) to be commanded to a different microcontroller on the DM. Feedback about the status of the DM is sent back up the chain in reverse direction.

According to FIG. 9, spray settings architecture 900 enables disinfection module 922 to communicate with components of main computer 920. DM board 922 of disinfection module (DM) 922 communicates bi-laterally (i.e., in both directions) with DM node 914 of main computer 920. DM node 914 further a DM interface 918 and DM manager 916. DM node 914 also communicates bi-laterally with Safety Health Node 902, consisting of Robotic Interface API 904 and UI Node 906 consisting of Robot Interface API 908. Furthermore, Plan 910 and Avidbots Command Center (ACC)/Telemetry 912 act as further inputs to architecture 900 and feeds into UI node 906. Plan 910 represents the autonomous software control of the disinfection module. ACC/Telemetry 912 represents the ability to remotely control and view the status of the disinfection module.

According to FIG. 9, Plan 910 represents the autonomous software control of the disinfection module and ACC/Telemetry 912 represent the ability to remotely control and view the status of the disinfection module.

Figure 10:
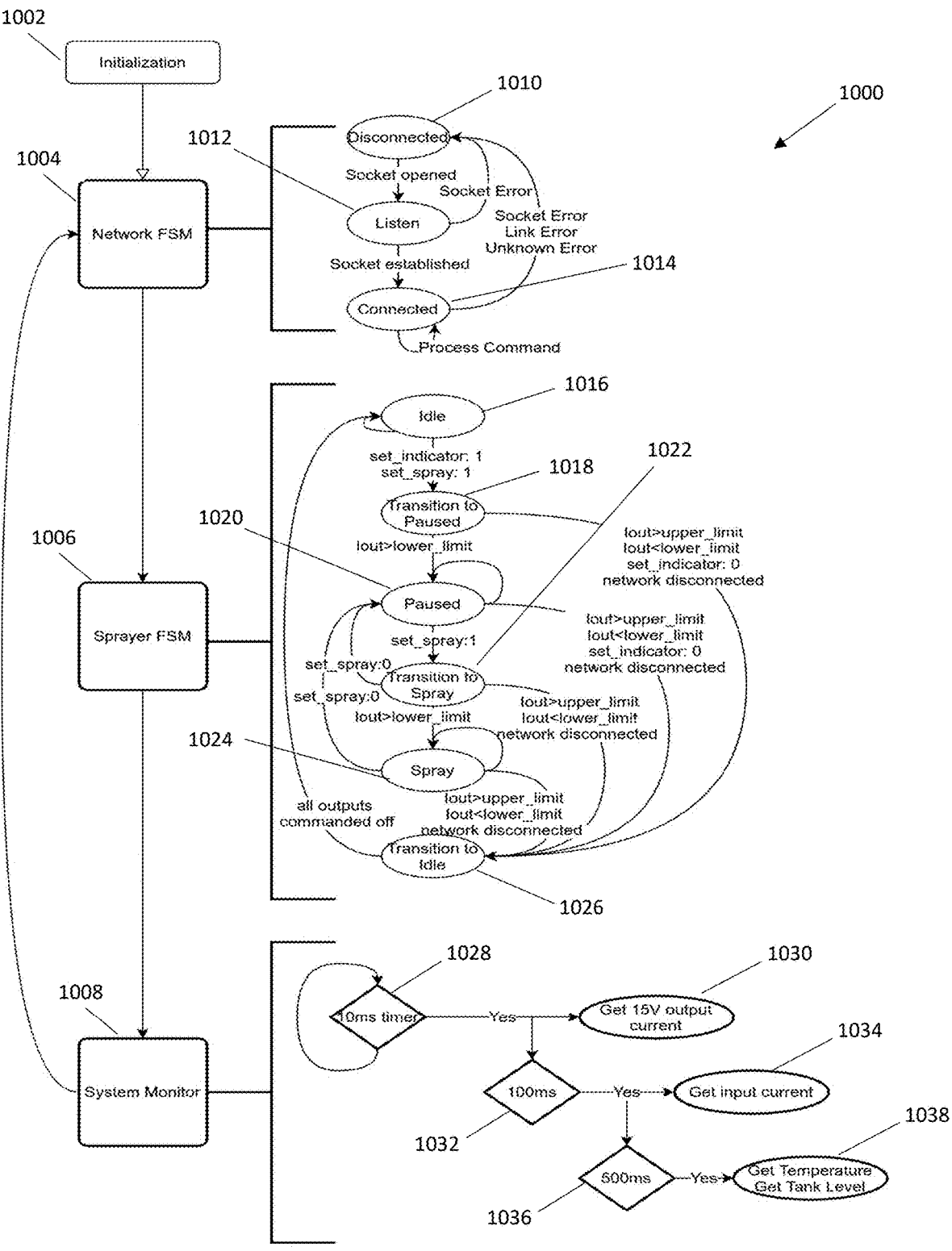
FIG. 10 is a diagram illustrating an exemplary architecture for the disinfection module consolidating all the sources of the spray into a single "high level node" representation.

FIG. 10 is a diagram illustrating an exemplary architecture for the disinfection module consolidating all the sources of the spray into a single "high level node" representation. According to FIG. 10, architecture 1000 begins with initialization step 1002 which connects to a Network Finite State Machine (FSM) 1004, Sprayer FSM 1006 and System Monitor 1008.

According to FIG. 10, Network FSM 1004 further comprises the step of monitoring for a Disconnected state at step 1010. If a socket is opened, then it will continue to Listen at step 1012. If there is a socket error, step 1012 will loop back to the Disconnected state at step 1010. However, if a socket is established, then it moves onto a Connected state at step 1014 whereby a command is processed. However, if there are any errors (e.g., socket error, link error, unknown error) at the connect state at step 1014, then the system loops back to the Disconnected state at step 1010.

According to FIG. 10, Sprayer FSM 1006 further comprises the initial Idle state 1016, where it moves to the state Transition to Paused at step 1018 where the system will set the indicator and spray settings. At step 1018, if the I-out, representing the measure output current (in amps), is greater than the lower limit, the system moves onto the Paused state at step 1020. Otherwise at step 1018, if the network is disconnected, I-out is greater than upper limit, I-out is less than lower limit, then set the indicator to zero, the system moves to transition to ideal step 1026.

According to FIG. 10, at the Paused step 1020, set spray is set to one which moves to the transition to spray step 1022. Otherwise at step 1020, if network is disconnected, I-out is greater than upper limit, I-out is less than lower limit, then set the indicator to zero, the system moves to transition to ideal step 1026.

According to FIG. 10, at the Transition to Spray step 1022, if the set spray is zero, the system loops back to the Paused step 1020. At step 1022, if I-out is greater than the lower limit then the setting moves to the spray step 1024. Otherwise at step 1022, if network is disconnected, I-out is greater than upper limit, I-out less than lower limit, the system moves to transition to ideal step 1026.

According to FIG. 10, at the Spray step 1024, if the set spray is zero, the system loops back to the Paused step 1020. Otherwise at step 1022, if network is disconnected, I-out is greater than upper limit, l-out less than lower limit, the system moves to transition to ideal step 1026. According to FIG. 10, at the Transition to Idle step 1026, all output commands are set to off and then the system loops back to Idle state at step 1016.

According to FIG. 10, System Monitor 1008 includes a further decision state to monitor 10 ms timer at step 1028. If the system doesn't meet this condition, the system continues to monitor for this condition at step 1028. However, if the system meets the 10 ms timer, then the system retrieves the 15V output current at step 1030. Furthermore, the system then monitors for a 100 ms timer at step 1032. If the system meets the 100 ms criteria, then it retrieves the input current at step 1034 and monitors for a 500 ms timer. If the system meets the 500 ms timer criteria, then it retrieves the temperature and tank level readings at step 1038.

Figure 11:
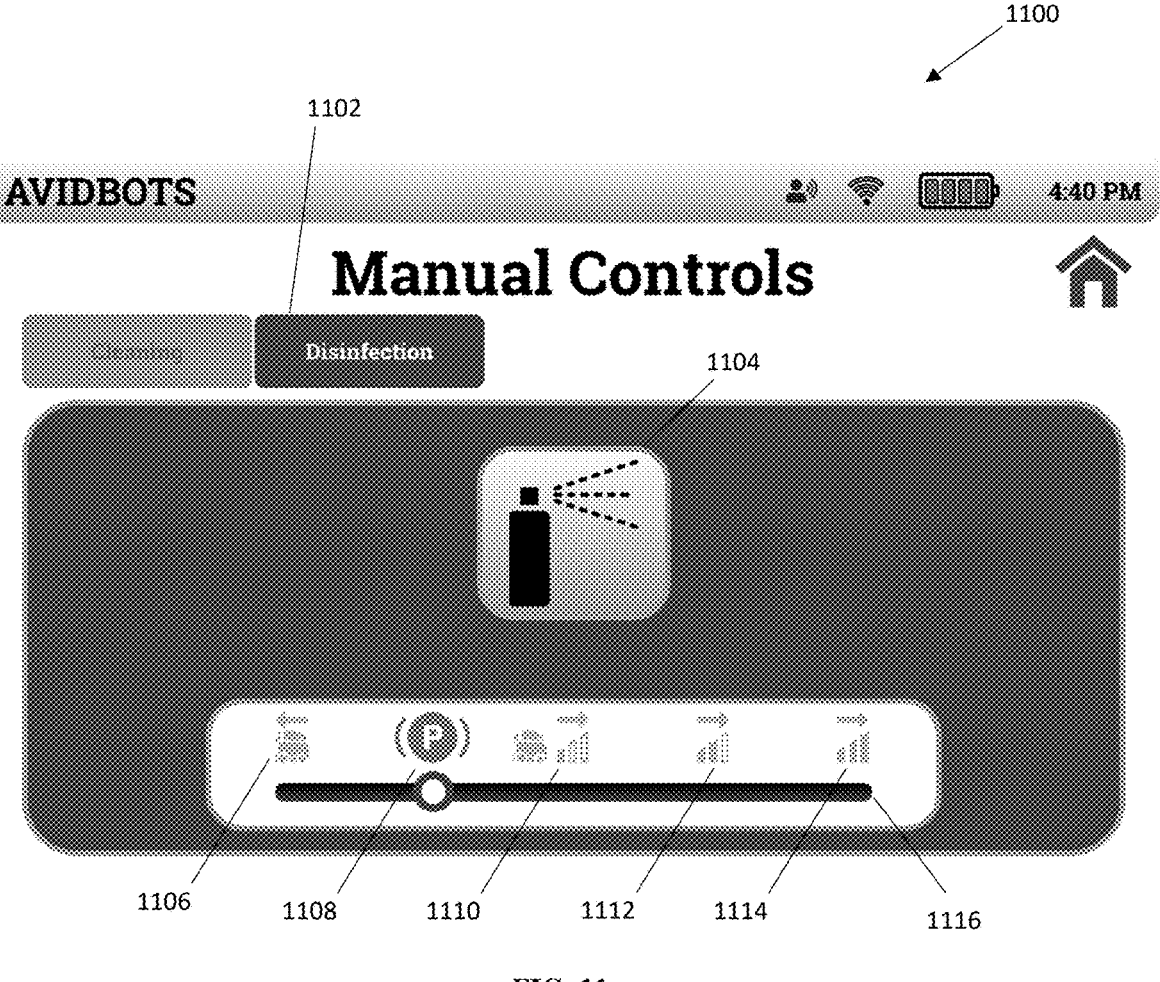
FIG. 11 is a diagram illustrating a manual control graphical user interface (GUI).

FIGS. 11 to 17 are diagrams illustrated snapshots of disinfection module graphical user interface (GUI). FIG. 11 is a diagram illustrating a manual control graphical user interface (GUI). According to FIG. 11, manual control GUI 1100 shows manual controls for Disinfection 1102 operations including a Disinfection icon 1104 and icons for different modes of operation of the cleaning device including reverse 1106, park 1108, $1^{st}$ gear 1110, $2^{nd}$ gear 1112 and $3^{rd}$ gear 1114. According to FIG. 11, the cleaning device is set at park 1108 with a slider icon 1116 indicating the current state of operation.

Figure 12:
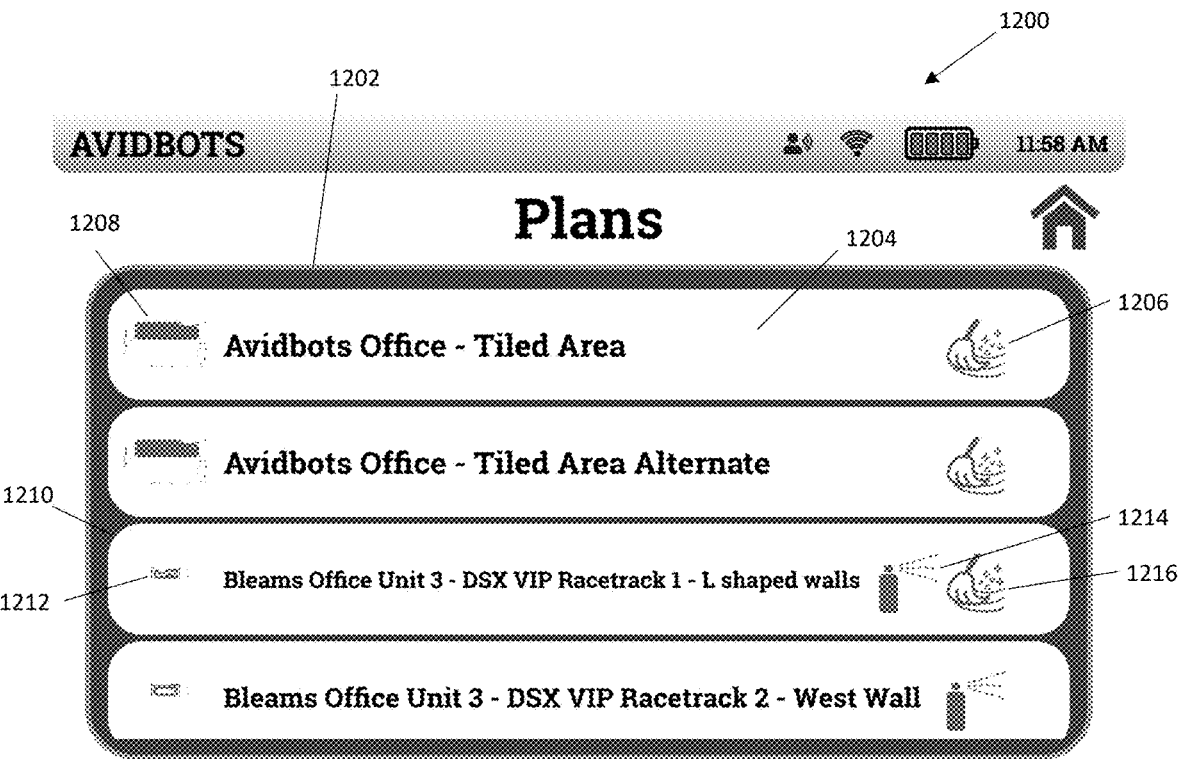
FIG. 12 is a diagram illustrating a GUI showing different cleaning or disinfecting plans.

FIG. 12 is a diagram illustrating a Disinfect Combo Selection GUI illustrating different cleaning or disinfecting plans. According to FIG. 12, Disinfect Combo GUI 1200 includes multiple cleaning plans 1202. According to FIG. 12, cleaning plan 1204 (i.e., Avidbots Office—Tiled Area) is shown to include a cleaning icon 1206 and a map icon 1208. A further combined cleaning and disinfecting plan 1210 (i.e., Bleams Office Unit 3—DSX VIP Racetrack 1) further includes a map icon 1212 and icons for disinfection 1214 and cleaning 1216.

Figure 13:
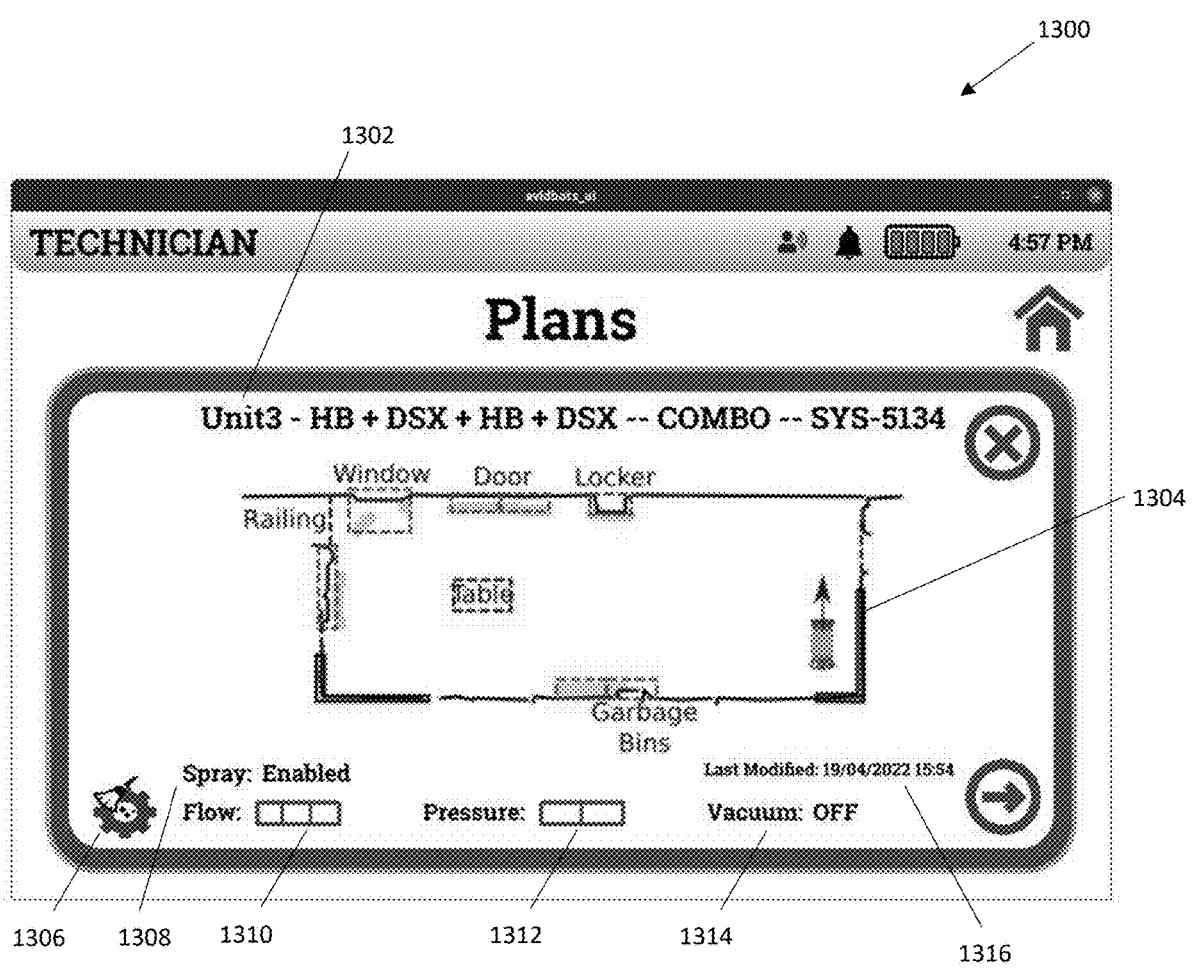
FIG. 13 is a diagram illustrating a selection of a Disinfect Combo GUI.

FIG. 13 is a diagram illustrating a selection of a Disinfect Combo Selected GUI. According to FIG. 13, Disinfect Combo Selected GUI 1300 is shown with a specific plan 1302 (e.g., Unit 3, SYS-5134) showing a building layout 1304 and features or settings selected. According to FIG. 13, Disinfect Combo Selected GUI 1300 also includes gear settings icon 1306, spray indicator 1308 (e.g., Enabled), flow indicator 1310, pressure indicator 1312, Vacuum indicator (e.g., Off) and time/date stamp 1316.

Figure 14:
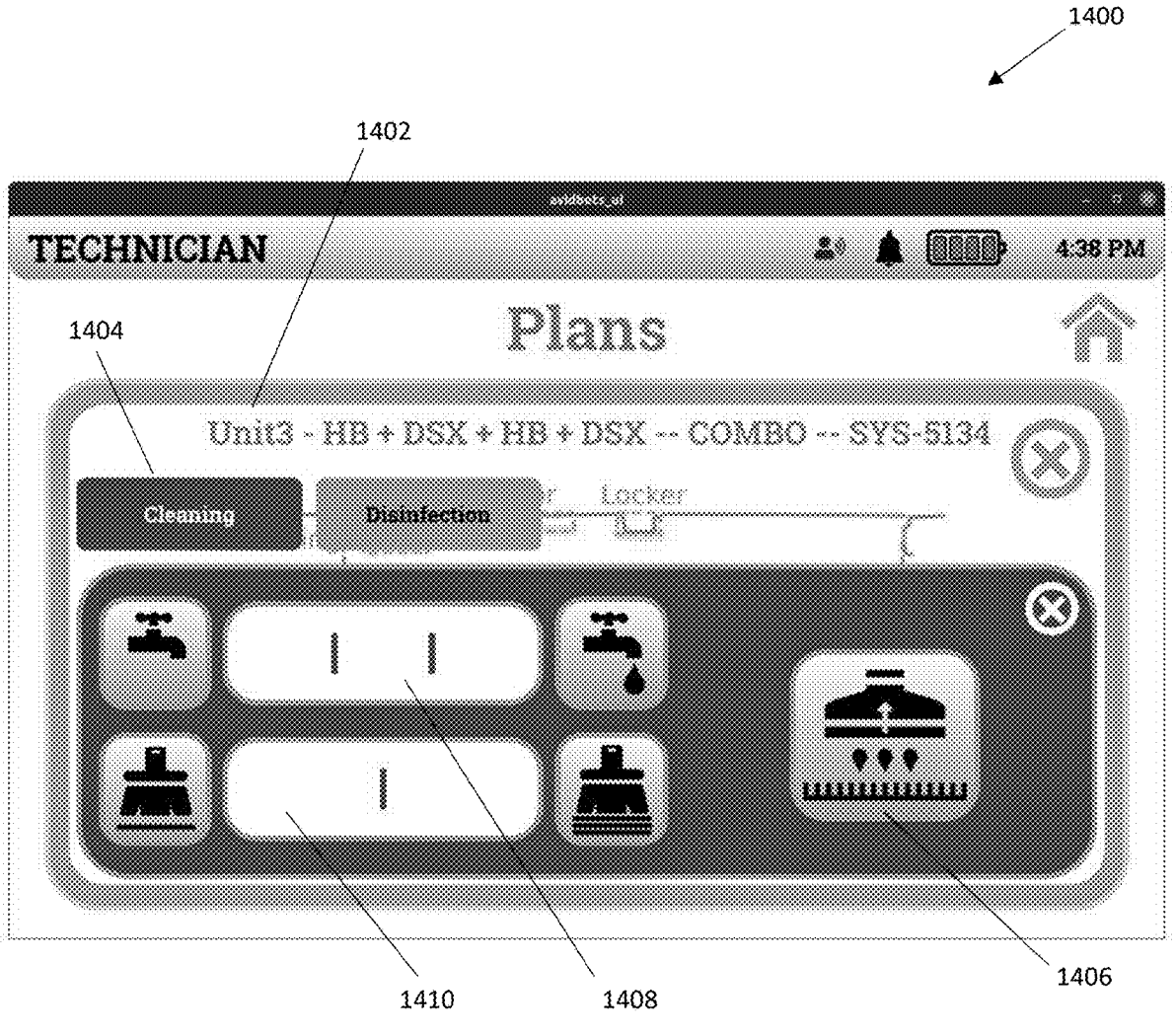
FIG. 14 is a diagram illustrating a Disinfect Combo GUI with clean settings selected.

FIG. 14 is a diagram illustrating a Disinfect Combo GUI with clean settings selected from the gear settings icon 1306. According to FIG. 14, Disinfect Combo Cleaning Setting GUI 1400 includes cleaning settings tab 1404 with vacuum 1406, cleaning plan 1402 (e.g., Unit 3— SYS-5134) and gauge indicators for water level 1408 and cleaning intensity 1410.

Figure 15:
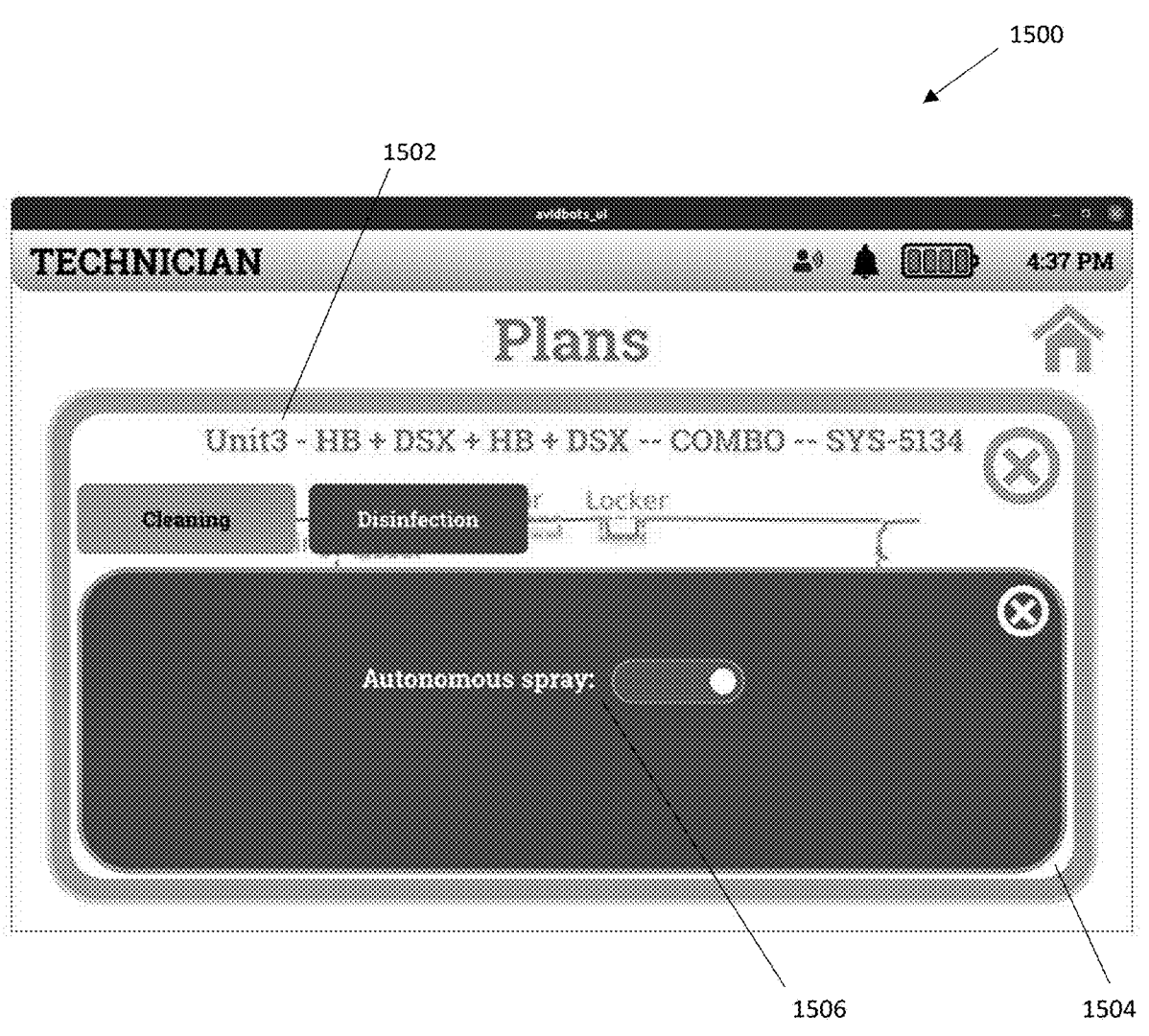
FIG. 15 is a diagram illustrating a Disinfect Combo GUI with a spray setting selected.

FIG. 15 is a diagram illustrating a Disinfect Combo GUI with spray setting selected. According to FIG. 15, Disinfect Combo GUI with spray setting 1500 further includes cleaning plan 1502 (e.g., Unit 3—SYS-5134) with a popup 1504 indicating Autonomous spray selection 1506.

Figure 16:
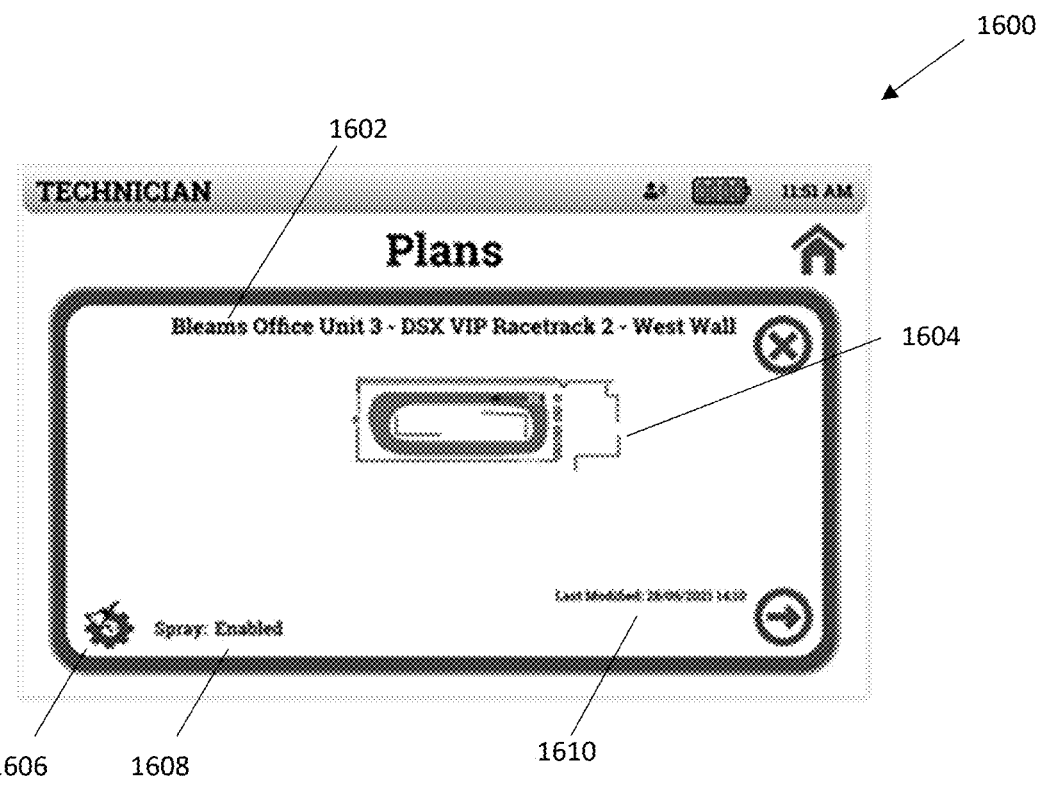
FIG. 16 is a diagram illustrating a Disinfection Plan confirmation screen on a GUI.

FIG. 16 is a diagram illustrating a Disinfection Plan confirmation screen on a GUI. According to FIG. 16, Disinfection Plan GUI 1600 includes a specific plan 1602 (e.g., Bleams Office Unit 3) showing a building layout 1604 and features or settings selected. According to FIG. 16, Disinfection Plan GUI 1600 also includes gear settings icon 1606, spray indicator 1608 (e.g., Enabled) and time/date stamp 1610.

Figure 17:
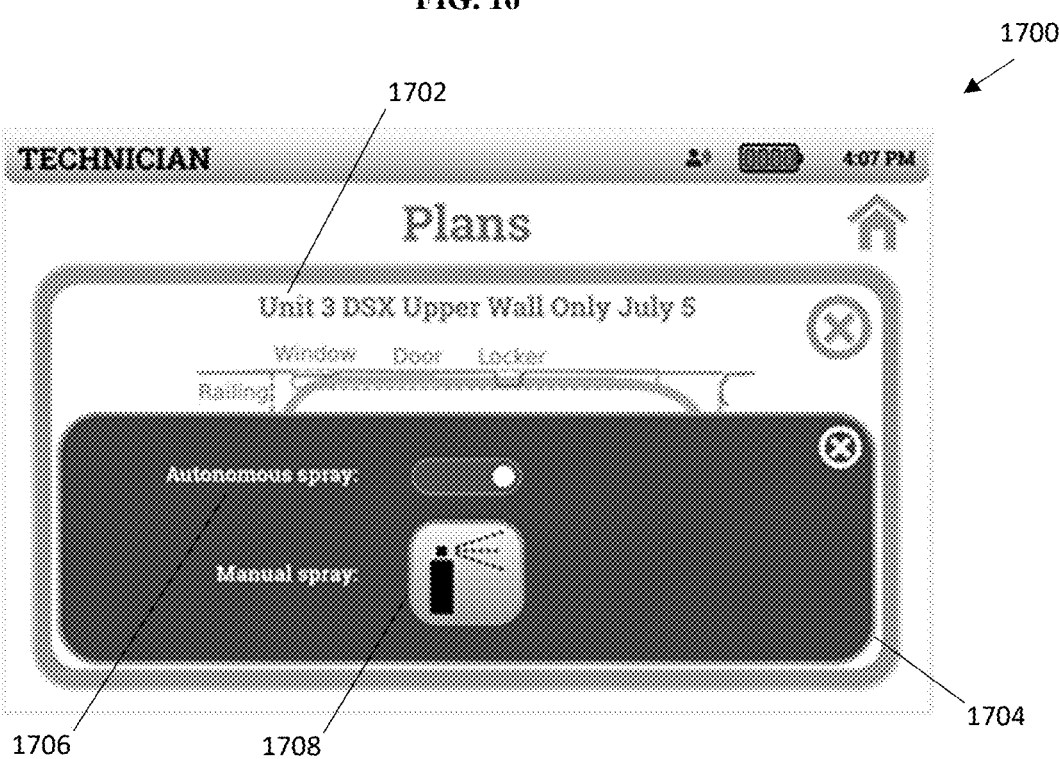
FIG. 17 is a diagram illustrating a state plan disinfection popup GUI.

FIG. 17 is a diagram illustrating a Disinfection Plan disinfection settings popup GUI. According to FIG. 17, Disinfection Plan disinfection popup GUI 1700 includes a specific plan 1702 (e.g., Unit 3 DSX Upper Wall), a popup 1704 having selections for Autonomous spray 1706 (e.g., slider for enable/disable) and Manual spray icon 1708.

Additional Features:

This disclosure describes a separate controller board for the disinfection module to directly control the low-level states of the disinfection hardware via current outputs to the constituent parts of the sprayer electromechanical assembly. This board accepts commands over an Ethernet communication from the autonomy computer.

1. High-Level Autonomy Control Software:

For adjusting the position, orientation, and speed of the cleaning device, the software consists of logic that computes and then subsequently executes control commands to follow a smooth deceleration from a high inter-target travel speed between targets, to a precise yet lower speed needed for smooth and even application of disinfectant on the target surface. The point at which the sprayer activates depends on the dynamically-planned trajectory of the cleaning device, accounting for the curvature of the reference path and adjusted on-the-fly at >1 Hz according to the presence of obstructions along the path. The reference path, which is a path that orients the cleaning device in order to spray targets at a constant distance, is provided by an external source, which can be manually- or automatically-generated. The targets are currently manually-specified as vector polygons on a map.

2. Detection of Sufficient Proximity Between Trajectory and Target to Trigger Spraying:

Using an internal simulation of future positions of the cleaning device given the appropriate future control command to track the reference trajectory, and evaluating whether the spray geometry (ellipse, cone, or similar, which is in a fixed position relative to the cleaning device) would intersect the target geometry (using a 2-D top-down repre-sentation of the environment), the precise time steps at which the cleaning device would need to trigger the audio announcement and deceleration can be determined. If the dynamic trajectory does not lead to intersection of the spray geometry with the target geometry, the cleaning device will not spray even if the reference path would do so. This is to account for dynamic obstacle avoidance. Consideration for the side of the cleaning device that the sprayer is aimed at is provided by the precise spray geometry.

In a future implementation, targets and non-targets could be recognized using a machine learning multi-class segmentation algorithm or similar to automatically enable or disable the sprayer as appropriate.

3. Adjusting the Flow of the Spray to Handle Curved Paths:

According to a further embodiment, the above controls the sprayer's on/off status, but does not mention flow rates. The implementation in 1 assumes a constant spray rate. However, when the cleaning device slows down for curves, and also because the effective speed of the spray during turns varies (inside turns vs outside turns result in different deposition rates per unit area, in litres/square metre), flow control is important to avoid over- or under-saturating the target surface. To produce a constant deposition rate, calculate and command an appropriate flow rate to a PWM-controlled pump for example, based on the desired deposition rate per unit area of coverage given the cleaning device's projected speed.

4. Adjusting the Flow of Spray Per Target:

According to a further embodiment, the system allows custom settings for each target to adjust either the flow rate or the deposition rate per unit area. This is useful if some targets need a greater amount of spray deposited. The software will then automatically calculate if necessary, and command the desired flow rate.

5. Nuances to Autonomous Perception:

Since the spray can be visible at times to the lidar, for example, an IR intensity-based filter can be applied to prevent mist-induced lidar returns from interfering with the collision safety detection system of the cleaning device.

6. Hardware/UI Coordination Elements:

Before the start of spray, the cleaning device must also coordinate an audible alert or audible signal and announcement via the device's onboard loudspeakers, signifying the spray is about to begin. This needs to be triggered while the cleaning device is travelling at speed, so the announcement duration is factored into the start trigger as a function of the projected velocity profile of the cleaning device. At the same time, an illuminating LED array at the end of the sprayer apparatus, aimed at the spray target, can be coordinated to turn on at the start, and off at the end of spraying. The command can be in the form of a publisher-subscriber topic between the higher-level autonomy and lower-level spray control processes.

7. Feedback and Diagnostics:

Feedback allows the cleaning device to continue with the misting activity if the module is in nominal operation. Diagnostics regarding the module are fed back to the software to decide if it needs to stop movement, or inform the user to address a physical issue with the cleaning device, such as pump current issue due to a blown fuse, communication issues between the hardware modules, or low disinfectant volume. The user can be a remote operator who can handle software-addressable faults, or a ground operator who can handle faults of a more hardware nature.

8. Operator Overrides:

During autonomous spraying, it is possible for the cleaning device operator to pause autonomous spraying, or locally override the sprayer state to be on or off. The remote operator can also remotely disable the sprayer, or enable the autonomous spraying mode. (For safety reasons, due to lack of visual confirmation, network delays, network dropouts, etc., the remote operator cannot actually trigger the spraying activity on/off directly.)

9. Safety Features:

Safety features include: not spraying if the cleaning device path deviates too far from the target due to obstacle detection, or if the cleaning device's localization or tracking are poor. Other safety states of the cleaning device, such as when the emergency button is pressed, will also stop the sprayer. Furthermore, the audible alert or audible signal and the illuminating LED array at the end of the sprayer apparatus can also be considered a safety feature.

10. Reporting Features:

Reporting features keep track of where the sprayer has been active on the global map. It tracks how much spray coverage overlap with the targets was achieved, and other metrics of the cleaning device's performance such as time spent spraying each target, overall time, number of and identities of successful and missed spray targets, and amount of disinfectant consumed. It identifies the start and end times of targets visited. It identifies the amount of spray deposited for each target. Spray coverage area can be tracked on a bitmap as the spray geometry is traced and interpolated over the bitmap, then later the coverage rate can be determined from the number of covered cells within each desired region to be covered.

11. An Overall Hierarchical Software Architecture:

Allows each layer of functionality of the software stack to handle independent logic and decision-making pertaining to their level of concern, and communicating only with neighbouring levels. At the lower level, this defines a common interface for allowing both manual, remote, and autonomous controls of the sprayer activation: the lower level software arbitrates the priority levels of each request to make a final decision. The final spray state is then commanded to the disinfection module controller board which applies current to the pump, LED, and electrostatic module. The intermediate level deals with generating the real-time trajectory accounting for obstacles, high-level safety, and the timing and trigger of the autonomous spray request. The higher level coordinates the sequence of targets visited. Other functions are differentiated by their focus, such as localization, obstacle detection, telemetry, safety, diagnostics etc.

12. Configurable Software for Multiple Applications:

According to further embodiments of the disclosure, the system may have a module design. The same software build installation can be used to allow variations of cleaning devices to perform disinfection (if the module exists), side-sweeping, and cleaning. This is enabled via configuration, done on a fleet management website for all Neo™ cleaning devices.

13. Architecture that Permits Concurrent Missions:

According to a further embodiment, the system may also include an architecture that permits concurrent missions (e.g., cleaning while disinfecting). The planning and control software can simultaneously consider the requirements of both cleaning and disinfecting to enable spraying on cleaning passes. Path planning that ensures disinfection coverage can leverage a spiral tour pattern that ensures outside walls are visited with the sprayer facing the correct side, while the wall distance is configurable to permit the desired spray pattern. It provides tooling to specify missions that can perform both tasks. It has unique UI and display characteristics for filtering and showing missions and reports of mixed missions.

14. Automatic Pitch Control:

To enable the cleaning device to automatically spray targets at different elevations off the floor, ranging from benches at sitting height to lockers at shoulder height, an automatic sprayer end effector pitch control system is described below.

In one instantiation, the pitch control system contains a DC motor for pitch control. The motor is attached to an axle affixed to the end effector. The axle is held in place by rotary bearings mounted via a bracket on the robot chassis. The motor can be commanded to specific angular positions or undergo various velocity profiles to achieve a range of static or dynamic spraying patterns.

These commands are provided via Ethernet from the high-level software on the main computer, to a motor controller board that applies the motor current provided by cleaning device's primary battery via a power cable. Alternatively, data signal can also be provided from the disinfection module control board to a separate motor driver board attached to the motor itself.

These angles can point the end effector down towards the floor or up towards the ceiling, with a range of +15/−45 degrees from the horizontal plane. Furthermore, there may also be strain-relief or motion-guiding/limiting mechanical features for the hose and electrical cord if these need to constantly undergo automatic pitch adjustment. Additionally, this automatic pitch control may also replace the manual knobs of the disinfection module configured for manual pitch adjustment as these manual knobs may be deemed redundant and conflict with the motor's pitch adjustment.

During manual operation, the pitch can be controlled by the operator using the cleaning device's graphical user interface (GUI) by selecting the desired pitch angle via a slider interface element (i.e., by 5, 10, 15 degree increments). Similarly, in the diagnostics page on the GUI, the pitch can be controlled via a slider, with potentially the same or finer increments, to ensure nominal operation by a service technician.

The pitch can also be adjusted automatically during an autonomous disinfection plan by applying one or more preset angles or speed profiles specified for each target. This specification comes from the disinfection plan prepared and provided in advance of the disinfection mission. The angle of the sprayer will be automatically commanded by the software and adjusted at the pitch control motor prior to initiation of the spray as the robot is driving, based on the time required to execute the change in the pitch angle.

In a further embodiment, the end effector's up/down motion can be coordinated with the horizontal motion of the robot to achieve wave-like spraying patterns at various amplitudes and periods, and variable wave shapes not limited to sinusoids or step functions. The flow rate of the sprayer can be coordinated with the pitch angle to account for variation in the distance to the target due to the height of the target, to achieve a desired concentration per unit area of disinfectant. If multiple pitch specifications are provided for a single target, this will in turn result in multiple passes of the cleaning device over the same target following the same or similar paths. The pitch angle can be reported both to the remote operator, as well as recorded, in the disinfection coverage metrics report for disinfection operation tracking/reporting purposes.

According to the disclosure, there are multiple differentiators of this disclosure with existing systems. These differentiators include:

Manipulators move in a fixed volume of space, so the challenges are how to manipulate joints to cover a 3-D target. A planar cleaning device spraying platform needs to consider how to move the wheel on the ground to orient the sprayer attached on a platform mounted above the wheels.

Blanket coverage disinfection cleaning devices do not need to orient the sprayer. Therefore, they can do very simple back-and-forth or similar coverage. On the other hand, our solution strategically targets only the high-touch surfaces to minimize disinfectant used and overspray, and is more challenging because the path must account for the sprayer's orientation and their placement around the environment, and the speed at which the cleaning device can visit all of these targets.

According to embodiments of this disclosure, a semi-autonomous cleaning apparatus for cleaning surfaces is disclosed. The semi-autonomous cleaning apparatus comprises a frame supporting at least one storage volume, a drive system supported by the frame and configured to move the frame along a surface, a cleaning assembly coupled to the frame and configured to transfer debris from the surface to the at least one storage volume as the drive system moves the cleaning assembly along the surface, a front or rear sensing module comprising a plurality of sensors capable of computing and guiding the path and direction of the cleaning apparatus, a disinfection module to spray a disinfectant solution, an electronics system supported by the frame and including at least a memory and a processor, the processor being configured to execute a set of instructions stored in the memory and receiving input from the front and rear sensing module to perform at least one or more actions in relations to the disinfection module and a disinfection software module configured to control the disinfection module, an electronic display configured to show a graphical user interface (GUI) of the different operating modes and plans of the disinfection module, and a LIDAR sensor module in communication with the disinfection module configured to support the different operating modes and plans of the disinfection module.

According to the disclosure, the electronic display is a touchscreen display and the operating mode is selected from a cleaning mode and a disinfection mode. Furthermore, the disinfection mode further comprising selecting autonomous spray or manual spray. The GUI of the electronic display is configured to display icons associated manual controls, a selection of cleaning plans, icons associated with spray settings, building layouts (i.e., maps of the building facility) and icons associated with clean settings.

According to the disclosure, the LIDAR sensor module of the semi-autonomous cleaning apparatus further comprises modular plugins that can apply different measurement filters, such as an intensity filter for filtering spray noise, which can be toggled on/off from external triggers such as spray on/off for safety reasons to only activate the filter when spraying to avoid false negatives (i.e., filtering out real obstacles).

According to other aspects of the disclosure, a method of controlling a disinfection module of a semi-autonomous cleaning apparatus is disclosed. The method is configured to spray a disinfection solution and comprises the steps of initializing the disinfection module, monitoring a network Finite State machine (FSM) for network errors to establish a connection, monitoring a sprayer Finite State machine (FSM) and execute spray settings based on sprayer thresholds and monitoring system monitor settings and execute system monitor commands based on system monitor thresholds.

According to the disclosure, the network errors of the method further comprise a socket error, a link error and an unknown error. The sprayer thresholds of the method are selected from a list consisting of set indicator, set spray, I-out>lower limit, I-out>upper limit, I-out<lower limit and network disconnected. Furthermore, the system monitor commands of the method are selected from a list consisting of retrieving output current, retrieving input current, retrieving temperature and retrieving tank water level. The system monitor thresholds of the method are selected from a list consisting of 10 ms timer, 100 ms timer and 500 ms timer.

According to further aspects of the disclosure, a method of operating a disinfection module on a semi-autonomous cleaning device is disclosed. The method comprises the steps of logging into the semi-autonomous cleaning device, displaying a home screen graphical user interface (GUI) screen, displaying a choice of a manual operation or plan operation mode, if the plan list operation mode is selected, displaying a plan checklist GUI screen, selecting an operating plan, executing the operating plan, providing a notification message of "Disinfection Started", executing the disinfection plan, and providing a notification message of "Disinfection ended" once the plan has been completed, and if the manual operation is selected, providing GUI icons on GUI screen for the user to manually execute operation and disinfection of the semi-autonomous cleaning device.

According to the disclosure, the GUI icons on the GUI screen of the method are configured to display icons associated with manual controls, a selection of cleaning plans, icons associated with spray settings, building layouts (i.e., including map of the building facility) and icons associated with clean settings. Furthermore, the disinfection plan of the method further comprising selecting autonomous spray or manual spray.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor. A "module" can be considered as a processor executing computer-readable code.

A processor as described herein can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. In some embodiments, a processor can be a graphics processing unit (GPU). The parallel processing capabilities of GPUs can reduce the amount of time for training and using neural networks (and other machine learning models) compared to central processing units (CPUs). In some embodiments, a processor can be an ASIC including dedicated machine learning circuitry custom-build for one or both of model training and model inference.

The disclosed or illustrated tasks can be distributed across multiple processors or computing devices of a computer system, including computing devices that are geographically distributed.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

While the foregoing written description of the system enables one of ordinary skill to make and use what is considered presently to be the best mode thereof, those of ordinary skill will understand and appreciate the existence of variations, combinations, and equivalents of the specific embodiment, method, and examples herein. The system should therefore not be limited by the above described embodiment, method, and examples, but by all embodiments and methods within the scope and spirit of the system. Thus, the present disclosure is not intended to be limited to the implementations shown herein but is to be accorded the widest scope consistent with the principles and novel features disclosed herein.

What is claimed:

1. A semi-autonomous cleaning apparatus for cleaning surfaces, comprising:

a frame with at least one storage volume within;

a drive system supported by the frame and configured to move the frame along a surface;

a cleaning assembly coupled to the frame at a lower portion of the frame and configured to transfer debris from the surface to the at least one storage volume as the drive system moves the cleaning assembly along the surface;

a front or rear sensing module comprising a plurality of sensors capable of computing and guiding a path and direction of the cleaning apparatus;

a disinfection module to spray a disinfectant solution, the disinfection module further comprising;

an automatic sprayer configured for spraying non-floor surfaces;

a tank configured to store the disinfectant solution;

a hose configured to connect the tank to the automatic sprayer;

a pump configured to move the disinfectant solution across the hose to the automatic sprayer;

and an automated pitch control system;

an electronics system supported by the frame and including at least a memory and a processor, the processor being configured to execute a set of instructions stored in the memory and receiving input from the front or rear sensing module to perform at least one or more actions in relation to the disinfection module;

an electronic touchscreen display configured to show a graphical user interface (GUI) of different operating modes and cleaning plans of the disinfection module; and a LIDAR sensor module in communication with the disinfection module configured to support the different operating modes and cleaning plans of the disinfection module; wherein the automatic sprayer and the automated pitch control system is configured to support the disinfection module to automatically spray targets at different elevations of non-floor surfaces;

wherein the automatic sprayer is located at a rear edge of a flat top surface of the frame that is parallel to a bottom edge of the cleaning assembly, wherein the flat top surface is opposite the lower portion of the frame;

wherein the tank of the disinfection module is an external tank and is housed at a rear surface of the frame;

wherein the disinfection module is configured to receive instructions for automated spraying of non-floor surfaces;

wherein the GUI of the electronic touchscreen display is configured to receive selection of the different operating modes and cleaning plans from an operator of the cleaning apparatus;

wherein a cleaning plan is executed autonomously upon selection and confirmation from the operator;

wherein the cleaning apparatus is configured to support simultaneous cleaning of floor surfaces and automated spraying and disinfecting of non-floor surfaces during cleaning passes of the apparatus; wherein the processor is configured to receive data from the LIDAR sensor module and the cleaning plans and provide instructions to the cleaning apparatus to navigate to a target location and to spray the disinfectant solution at the target location;

wherein the disinfection module is configured to monitor a sprayer Finite State Machine (FSM) and execute spray settings based on automatic sprayer thresholds;

wherein the automated pitch control system further comprises an end effector to adjust the automatic sprayer to different angles and positions for precision autonomous control.

2. The semi-autonomous cleaning apparatus of claim 1 wherein the operating mode is selected from a cleaning mode and a disinfection mode.

3. The semi-autonomous cleaning apparatus of claim 2 wherein the disinfection mode further comprises selecting autonomous spray or manual spray.

4. The semi-autonomous cleaning apparatus of claim 1 wherein the GUI of the electronic display is configured to display icons associated with manual controls, a selection of cleaning plans, icons associated with spray settings, building layouts and icons associated with clean settings.

5. The semi-autonomous cleaning apparatus of claim 4 wherein building layouts further include a map of a building facility.

6. The semi-autonomous cleaning apparatus of claim 1 wherein the LIDAR sensor module further comprises modular plugins that can apply different measurement filters, further comprising an intensity filter for filtering spray noise.

7. The apparatus of claim 6 wherein the intensity filter is configured to be toggled on or off from external triggers wherein the intensity filter is activated to avoid false negatives.

* * * * *